(12) United States Patent
Sohn et al.

(10) Patent No.: US 8,283,511 B2
(45) Date of Patent: Oct. 9, 2012

(54) ETHYLENE PRODUCTION BY STEAM CRACKING OF NORMAL PARAFFINS

(75) Inventors: Stephen W. Sohn, Arlington Heights, IL (US); Lynn H. Rice, Denver, CO (US); Santi Kulprathipanja, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 374 days.

(21) Appl. No.: 12/749,817

(22) Filed: Mar. 30, 2010

(65) Prior Publication Data

US 2011/0245556 A1    Oct. 6, 2011

(51) Int. Cl.
*C07C 7/12* (2006.01)
(52) U.S. Cl. ......... 585/826; 585/825; 585/820; 585/648
(58) Field of Classification Search .................. None
See application file for complete search history.

(56) References Cited

U.S. PATENT DOCUMENTS

| | | | |
|---|---|---|---|
| 3,208,833 A | 9/1965 | Carson | |
| 3,214,347 A | 10/1965 | Grekel et al. | |
| 3,291,726 A | 12/1966 | Broughton | |
| 3,392,113 A | 7/1968 | De Rosset | |
| 3,455,815 A | 7/1969 | Fickel | |
| 3,523,762 A | 8/1970 | Broughton | |
| 3,617,504 A | 11/1971 | Berg | |
| 4,006,197 A | 2/1977 | Bieser | |
| 4,061,724 A | 12/1977 | Grose et al. | |
| 4,133,842 A | 1/1979 | Anderson | |
| 4,402,832 A | 9/1983 | Gerhold | |
| 4,434,051 A | 2/1984 | Golem | |
| 4,455,444 A | 6/1984 | Kulprathipanja et al. | |
| 4,498,991 A | 2/1985 | Oroskar | |
| 5,026,951 A * | 6/1991 | Schmidt et al. ............... 585/738 |
| 5,262,144 A | 11/1993 | McCulloch | |
| 5,276,246 A | 1/1994 | McCulloch et al. | |
| 5,292,900 A | 3/1994 | Basha et al. | |
| 6,001,241 A | 12/1999 | Gosling et al. | |
| 6,013,173 A | 1/2000 | Bogdan | |
| 6,036,845 A | 3/2000 | Funk et al. | |
| 6,407,301 B1 | 6/2002 | Foley et al. | |
| 6,670,519 B1 * | 12/2003 | Sohn et al. ............... 585/826 |
| 2006/0205988 A1 * | 9/2006 | Rice et al. ............... 585/648 |

FOREIGN PATENT DOCUMENTS

GB    2 119 398    3/1983

OTHER PUBLICATIONS

Reddoch et al., "Separation of Normal Paraffins from Isoparaffins", Eleventh Australian Conference on Che. Engineering, Brisband, Sep. 4-7, 1983.

Flanigan et al., "Silicalite, A New Hydrophobic Crystalline Silica Molecular Sieve", Nature, vol. 271, Feb. 9, 2978.

* cited by examiner

*Primary Examiner* — Tam M Nguyen
(74) *Attorney, Agent, or Firm* — Maryann Maas

(57) ABSTRACT

A simulated moving bed adsorptive separation process for preparing the separate feed streams charged to naphtha reforming unit and a steam cracking unit has been developed. The feed stream to the overall unit is passed into the adsorptive separation unit. The desorbent in the adsorptive separation is C12 hydrocarbons. The simulated moving bed adsorptive separation separates the components of the feed stream into a normal paraffin stream, which is charged to the steam cracking process, and non-normal hydrocarbons which are passed into a reforming zone. The desorbent is readily separated from the normal paraffin stream and from the non-normal paraffin stream and the simulated moving bed adsorption zone is operated at an A/Fn ratio of from about 0.90 to about 0.92.

20 Claims, 2 Drawing Sheets

ETHYLENE PRODUCTION BY STEAM CRACKING OF NORMAL PARAFFINS

FIELD OF THE INVENTION

The invention relates to a simulated moving bed adsorptive separation process used to prepare a feed stream for a steam cracking process unit. The invention more specifically relates to a simulated moving bed adsorptive separation process for producing a high purity normal paraffin stream used as a feed stream to a steam cracking process. The adsorptive separation process uses a hydrocarbon desorbent having 12 carbon atoms and the adsorptive separation process is operated at an A/Fn ratio of about 0.90 to about 0.92.

BACKGROUND OF THE INVENTION

Steam cracking, which is the thermal cracking of hydrocarbons in the presence of steam, is used commercially in large scale industrial units to produce ethylene and to a lesser extent propylene. These pyrolysis units are often charged a naphtha boiling range feed stream. The typical petroleum derived naphtha contains a wide variety of different hydrocarbon types including normal paraffins, branched paraffins, olefins, naphthenes, benzene, and alkyl aromatics. It is known in the art that paraffins are the most easily cracked and provide the highest yield of ethylene and that some compounds such as benzene are relatively refractory to the typical cracking conditions. It is also known that cracking normal paraffins results in a higher product yield than cracking iso-paraffins. A paper entitled "Separation of Normal Paraffins from Isoparaffins" presented by I. A. Reddoch, et al, at the Eleventh Australian Conference on Chemical Engineering, Brisbane, Sep. 4-7, 1983 discloses that the ethylene yield of a cracking unit can be increased if it is charged a $C_5$ to $C_9$ stream of normal paraffins rather than a typical $C_5$ to $C_9$ natural gasoline.

The separation of the myriad components of a petroleum naphtha into specific structural types by fractional distillation, a form of fractionation, is expensive and complicated and any attempt to improve the character of the naphtha as a steam cracking feed employs other means which act on a class of structural types, such as extraction.

The benefits of separating the various classes of hydrocarbons in petroleum fractions have led to the development of a number of different techniques which separate the hydrocarbons by type rather than individual molecular weight or volatility. For instance, various forms of liquid extraction can be used to remove aromatic hydrocarbons from a mixture of aromatic and paraffinic hydrocarbons. Adsorptive separation techniques have been developed to separate olefins from paraffins and to separate normal (straight chain) paraffins from non-normal, e.g. branch chain paraffins and aromatics. An example of such a process is described in GB 2,119,398A which employs a 5 Å zeolite having crystals larger than 5 Å to selectively adsorb straight chain hydrocarbons to the exclusion of non-straight chain hydrocarbons and sulfur compounds.

There are great economic benefits to a large scale unit if an adsorptive separation is performed in a continuous manner. U.S. Pat. No. 4,006,197 and U.S. Pat. No. 4,455,444 describe techniques for performing a continuous simulated moving bed (SMB) adsorptive separation process for the recovery of normal paraffins, which is the preferred mode of operating the adsorptive separation zone of the subject invention. U.S. Pat. No. 4,006,197 describes the fractionation of the raffinate and extract streams to recover desorbent which is reused in the process.

U.S. Pat. No. 3,291,726 describes the use of simulated moving bed technology to separate normal paraffins from a petroleum derived fraction. U.S. Pat. No. 6,407,301 describes the use of simulated moving bed technology to separate normal paraffins from non-normal hydrocarbons to generate a feed to a steam cracking zone and a feed to a catalytic reforming zone. Both references further describe that a suitable desorbent for use in the process may be provided by fractional distillation of the feedstock and the raffinate and extract removed from the adsorption zone.

Having the desorbent used in the simulated moving bed generated by fractional distillation of the feedstock often results in a desorbent that has a boiling point fairly close to that of the components of the raffinate or extract. Separation and recycle of the desorbent may require more costly equipment, such as increased stages in distillation columns, and more utilities costs associated with the larger equipment. When using simulated moving bed technology to separate normal paraffins from non-normal hydrocarbons in order to generate a feed to a steam cracking zone and a feed to a catalytic reforming zone, employing a desorbent having a boiling point diverse from that of the components of the raffinate and extract streams and not present in the feed stream results in significant cost reductions. The raffinate column and the extract column may be reduced in size and the utilities consumption may be reduced. There is no need to vaporize the desorbent and so there is a reduced utilities consumption in the raffinate and extract columns. Also, the reflux ratio is reduced thereby conserving costs. As compared to other operations, the feed stream to the simulated moving bed need not be fractionated before being introduced to the simulated moving bed, thereby eliminating the costs associated with one fractionation column.

However, most importantly, the A/Fn ratio may be in the range of 0.90 to about 0.92 which is significantly less than a standard range of from about 1.0 to about 1.2. The effect of the significantly reduced A/Fn ratio is the ability to process more material with less adsorbent thereby reducing costs.

SUMMARY OF THE INVENTION

The invention is a simulated moving bed adsorptive separation process which reduces the cost of separating normal paraffins from a broad boiling point range naphtha hydrocarbon fraction. The invention provides an improved method for recovering a broad boiling mixture of normal paraffins which is highly suitable as a feed to a steam cracking unit intended to produce ethylene. It simultaneously produces a very desirable catalytic reforming feed stock. Overall cost reduction and process simplification are obtained in part by using selective adsorption to recover normal paraffins, with the desorbent used in the adsorption zone being a hydrocarbon containing 12 carbon numbers. The desorbent is readily separated from the process components. The simplified separation of the desorbent from the process components leads to reduced capital investment and reduced utilities costs. Further costs reductions are achieved by operating the simulated moving bed adsorption zone with an A/Fn ratio of from about 0.90 to about 0.92. The reduced A/Fn ratio allows for a reduction in the amount of adsorbent required which can lead to lower construction costs and lower operational costs in addition to lower adsorbent costs.

A broad embodiment of the invention may be characterized as a process for preparing a feedstream to be charged to a steam cracking unit, which process comprises passing a feed stream comprising $C_5$ to $C_9$ hydrocarbons including $C_5$ to $C_9$ normal paraffins into an adsorption zone of a simulated moving bed adsorptive separation zone operating at an A/Fn ratio of from 0.90 to 0.92 and selectively retaining normal paraffins on an adsorbent located in the adsorption zone to yield a raffinate stream comprising non-normal $C_5$ to $C_9$ hydrocarbons; passing a hydrocarbon desorbent having 12 carbon atoms into a desorption zone in the adsorptive separation zone as at least part of a desorbent stream and removing normal paraffins from adsorbent present in the desorption zone to yield an extract stream comprising $C_5$ to $C_9$ normal paraffins and desorbent; separating at least a portion of the extract stream in a fractionation zone into a process stream comprising $C_5$ to $C_9$ normal paraffins and another process stream containing desorbent; and passing the process stream comprising $C_5$ to $C_9$ normal paraffins into a cracking zone producing ethylene.

DETAILED DESCRIPTION OF THE INVENTION

Figure 1:
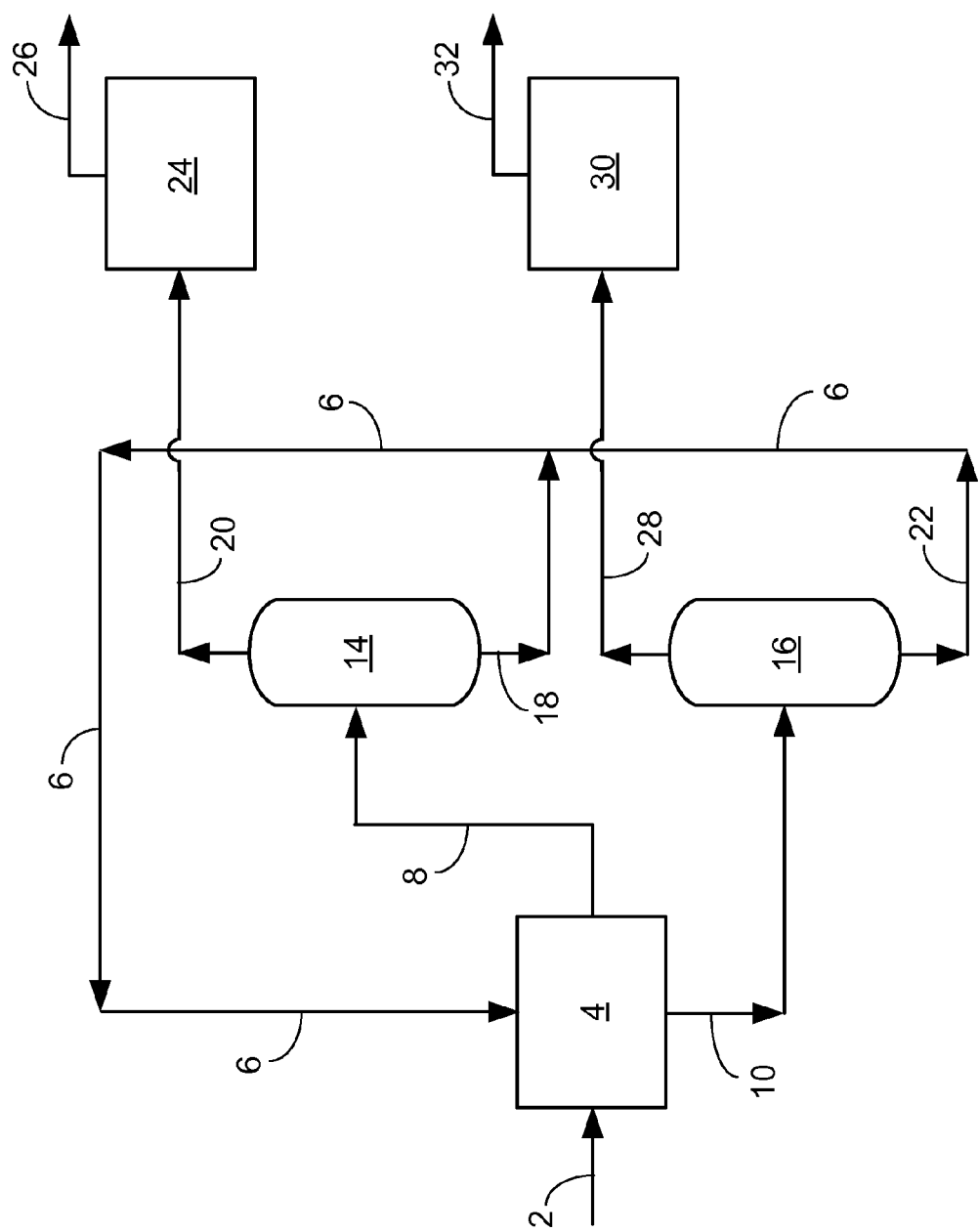
FIG. 1 is a simplified process flow diagram showing a naphtha feed of line 2 being divided into an extract stream and a raffinate stream in a simulated moving bed adsorptive separation zone. The extract and raffinate streams are each passed through a distillation column to separate desorbent. The resulting streams are passed to a steam cracking zone and a catalytic reforming zone, respectively.

The great bulk of the ethylene consumed in the production of various plastics and petrochemicals such as polyethylene is produced by the thermal cracking of higher molecular weight hydrocarbons. Steam is usually admixed with the feed stream to the cracking reactor to reduce the hydrocarbon partial pressure and enhance olefin yield and to reduce the formation and deposition of carbonaceous material in the cracking reactors. The process is therefore often referred to a steam cracking or pyrolysis.

It is known that the composition of the feed to the steam cracking reactor effects the results. A fundamental basis of this is the propensity of some hydrocarbons to crack more easily than others. The normal ranking of hydrocarbons tendency to crack to light olefins is normally given as normal paraffins; isoparaffins; olefins; naphthenes and aromatics. Benzene and other aromatics are particularly refractory and undesirable as cracking feedstocks, with only the alkyl sidechains being cracked to produce the desired product. The feed to a steam cracking unit is normally a mixture of hydrocarbons varying both by type of hydrocarbon and carbon number. This variety results in it being very difficult to separate less desirable feed components, such as aromatics, from the feedstream by fractional distillation. The aromatics can be removed by solvent extraction or adsorption. The present invention provides a process for upgrading (preparing) the feed to a steam cracking process unit while reducing the cost of removing non-normal hydrocarbons from a steam cracking process feed stream by simulated moving bed adsorptive separation.

Simulated moving adsorptive beds separation is used to separate the feedstream into a normal paraffin portion for the steam cracking unit and a non-normal fraction which is passed into a different conversion zone or withdrawn from the process. A hydrocarbon desorbent having 12 carbon atoms is used as the desorbent in the adsorptive separation zone. One desorbent is normal dodecane. With a C12 hydrocarbon desorbent, the separation of the feed components from the desorbent is more readily accomplished leading to reduced costs.

The feedstream to a steam cracking unit can be quite diverse and can be chosen from a variety of petroleum fractions. The feedstream to the subject process preferably has a boiling point range falling within the naphtha boiling point range or about 36° to 195° C. The simulated moving bed adsorptive separation process can handle diverse naphtha feeds compositions. The normal paraffin content has little impact on overall performance though process economics for naphthas dictate that a richer of high normal paraffin content feed is better. In general it is better that the naphtha feed carbon distribution does not overlap with the C12 desorbent since fractionation after the simulated moving bed enables the separation of desorbent components from the corresponding naphtha extract and raffinate streams. The separated desorbent is subsequently recycled to the simulated moving bed adsorptive separation process. Because of the carbon number of the desorbent herein, the ideal Naphtha feedstock to the simulated moving bed adsorptive separation process ranges from a nC5 to C11 range. In one embodiment, a $C_6+$ fraction is charged to the steam cracking zone, meaning that the feed stream is substantially free of hydrocarbons having five or fewer carbon atoms per molecule. In another embodiment the feed steam does not contain appreciable amounts, e.g. more than 5 mol-%, of $C_{12}$ hydrocarbons. A representative feed stream to the subject process is a $C_5$ to $C_{11}$ fraction produced by fractional distillation of a hydrotreated petroleum fraction. Hydrotreating is desired to reduce the sulfur and nitrogen content of the feed down to acceptable levels. A second representative feed is a similar fraction comprising $C_5$ to $C_9$ hydrocarbons. The feed will preferably have a carbon number range of at least three. It is within the scope of the subject invention that the feed stream to the process comprise only the heavier $C_6+$.

In general the simulated moving bed adsorptive separation adsorption zone operates at a temperature in general range from about 150° C. to about 187° C. with a specific embodiment of the invention ranging from about 170° C. to about 180° C. Adsorption conditions also preferred include pressures sufficient to retain process fluids in the liquid phase. Pressure can range up to 600 psig with a specific embodiment at 350 psig. Desorption zone conditions generally include the same temperature and pressure as used for adsorption conditions. Slightly different conditions may apply depending on the composition of the feed.

Since the extracted product from the simulated moving bed process is destined to be naphtha cracker feed to produce ethylene, high normal paraffin purity is not a critical requirement and a purity of greater than 95% is sufficient. The rejected product or raffinate from the simulated moving bed process is destined to be naphtha reformer feed. As such, a high normal paraffin recovery is not required with only a recovery greater than 90% desired. Ultimately process economics dictate the best combination of extract normal paraffin purity and recovery.

A significant advantage of the invention is the operation of the simulated moving bed adsorptive separation zone at an A/Fn ratio of about 0.90 to about 0.92. The A/Fn ratio available when using the C12 desorbent is significantly less than the traditional 1.0 to 1.2 A/Fn ratios. With this operating parameter being lower, less adsorbent is required to process a quantity of feed. Less adsorbent means less cost, including adsorbent costs and potentially reduced construction and operating costs.

In more detail, the key parameters to a simulated moving bed adsorption zone are the following zone parameters: A, $F_n$, and A/$F_n$. The first parameter, A, represents the selective pore rate measured in $m^3$/hr. For a set volume of adsorbent contained in the simulated moving bed adsorptive separation process chambers, there is a known selective pore volume. This selective volume quantity is divided equally among the various adsorbent beds. Since the simulated moving bed adsorptive separation process simulates a moving bed process where adsorbent moves counter current to the process flow, the selective pore rate represents the quantity of selective volume that moves with every step or index of the rotary valve. One step of the rotary valve indexes the feed point from one bed to the next sequential bed position. This indexing of the feed simulates the counter current movement of the adsorbent contained in one bed. The second of the simulated moving bed adsorptive separation process zone parameters is $F_n$. $F_n$ represents the volumetric rate of feed normals introduced to the simulated moving bed adsorptive separation process. The third simulated moving bed adsorptive separation process zone parameters is the ratio of A/$F_n$. A/$F_n$ is a unit-less value and represents the ratio of the selective pore rate (A) to the volumetric feed rate of n-paraffins ($F_n$). This ratio sets the amount of selective pores that circulate counter-current to the rate of feed normals introduced to the simulated moving bed adsorptive separation process. An A/$F_n$ value of 1.0 means an equal volume of selective pores is contacted to an equal volume of feed normal paraffins. If a simulated moving bed adsorptive separation process unit circulates more selective pores per unit of feed n-paraffins introduced (where A/$F_n$>1.0), greater normal paraffins recovery can be achieved. This phenomenon will continue until there is no benefit derived from the circulation of extra selective pore volume, or that A/$F_n$ increases will not increase paraffin recovery. This is due to inherent mass transfer limitation with the feed normal paraffins. Due to non-idealities introduced by the mechanical limitation of the simulated counter current moving bed, A/$F_n$ ratios normally employed in commercial units are greater than 1.0. From an economic viewpoint, lower A/Fn ratios are more desired since it results in lower adsorbent inventory and desorbent circulation and corresponding energy expense associated with desorbent fractionation from extract and raffinate products.

Referring now to the drawings, a naphtha boiling range feedstream having from $C_5$ to $C_9$ hydrocarbons enters the overall process through line 2 and is introduced to simulated moving bed adsorptive separation zone 4. The net bottoms stream is separated in the adsorptive separation zone by the selective retention of normal paraffins on a selective adsorbent located in that portion of the overall adsorptive separation zone dedicated to adsorption, which is referred to herein as an adsorption zone. These normal paraffins remain on the adsorbent until a stream of desorbent delivered from line 6 passes through the adsorbent. For this discussion the desorbent is selected to be a normal paraffin having 12 carbon atoms. The desorbent has properties which cause it to displace the feed normal paraffins resulting in the formation of a stream referred to herein as the extract stream. The extract stream comprises the normal paraffins, which were previously selectively retained on the adsorbent, and a quantity of the desorbent material. The extract stream is removed from the adsorptive separation zone 4 via line 8 and passed into a fractionation zone 14 referred to in the art as the extract column. This fractionation zone is designed and operated to separate the entering hydrocarbons into a net bottoms stream rich in the desorbent and a net overhead stream rich in the $C_5$ to $C_9$ normal paraffins of the extract stream. These normal paraffins are passed through line 20 into a steam cracking zone 24 operated at steam cracking condition effective to convert the paraffins mainly into ethylene removed from the process as a product stream of line 26.

In this embodiment, the less volatile heavier normal paraffin desorbent, C12, present in the extract stream is concentrated into the net bottoms stream removed from fractionation zone 14 in line 18. This paraffin stream is admixed along with a second stream of recycled heavier normal paraffin from line 22 into line 6. The total flow of heavier normal paraffin formed in this manner is passed into the adsorptive separation zone 6 as the desorbent stream.

During the adsorption step in the separation zone 4 the non-normal components of feed 2 pass through the adsorption zone unaffected and are removed from zone 4 via line 10 as a process stream referred to as the raffinate stream. The raffinate stream also contains $C_{10}$ or heavier normal paraffin which previously occupied the void spaces of the adsorbent bed(s) through which it has passed. This is desorbent left from the previous step in the separation cycle. The raffinate stream is passed into fractionation zone 16, referred to in the art as the raffinate column. The raffinate stream is separated in column 16 into a net bottoms stream of line 22 and a net overhead stream of line 28 referred to as the raffinate product stream. The bottoms stream is rich in $C_{12}$ normal paraffin and is recycled to the adsorptive separation zone 4 as desorbent. The overhead stream comprises an admixture of non-normal paraffins, aromatics and naphthenes and is passed into a catalytic reforming zone 30 for the production of high octane motor fuel components removed from the process via line 32.

Figure 2:
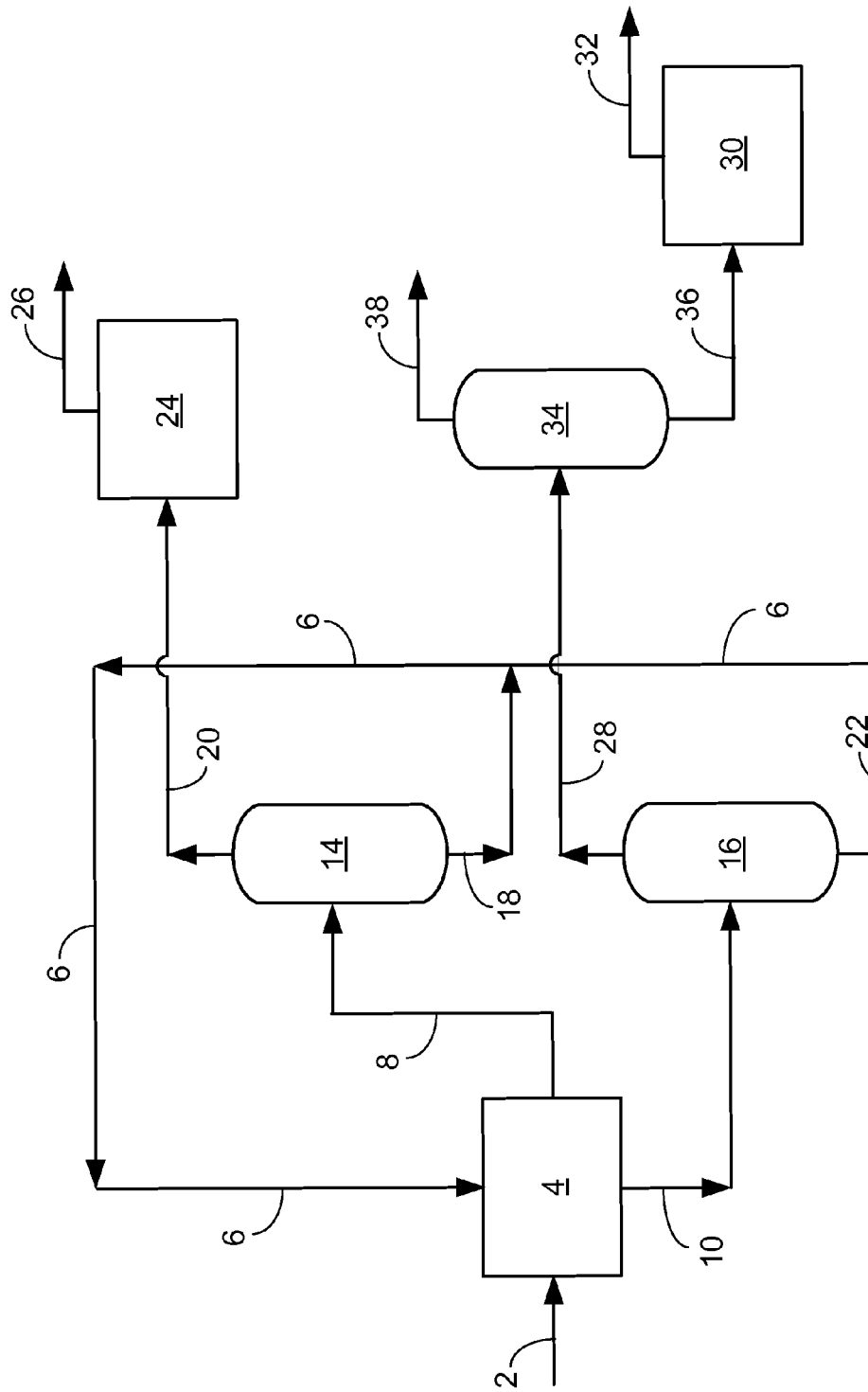
FIG. 2 is a simplified process flow diagram showing a naphtha feed of line 2 being divided into an extract stream and a raffinate stream in a simulated moving bed adsorptive separation zone. The extract and raffinate streams are each passed through a distillation column to separate desorbent. The raffinate column overhead is further fractionated to remove the lighter $C_5$, $C_6$, hydrocarbons. The resulting streams are passed to a steam cracking zone and a catalytic reforming zone, respectively.

The application of the subject invention to a petroleum refinery having existing catalytic reforming and cracking units which derive their feed from the same source can cause an imbalance in the available feed to the reforming zone. This is because it is necessary to make up for the removal of the normals from the feed stream of line 2. That is, it is necessary to increase the flow rate of line 2 to balance out the removal of normal hydrocarbons in zone 4 and maintain the same charge rate through line 20 to the cracking zone. With a normal distribution of hydrocarbon species this increases the amount of $C_6$+ feed generated for the reforming unit. To counteract this the raffinate stream of line 28 is fractionated to remove $C_5$, $C_6$, and $C_7$ acyclic paraffins. Turning to FIG. 2, this can be accomplished by passing the raffinate product stream into an optional fractional distillation column 34. The function of this column is to remove the lighter $C_5$, $C_6$, hydrocarbons and optionally some or all $C_7$ hydrocarbons via line 38. All of the $C_5$ and $C_6$ hydrocarbons are removed in this manner, but the fractionation is preferably adjusted to allow $C_7$ naphthenes to remain in the feed to the reforming zone. This degree of hydrocarbon removal is sufficient to normally counteract the increased rate of reformer feed generated by the overall process. This additional fractionation has synergistic effects. The $C_5$ to $C_7$ material which is removed is normally good quality gasoline blending stock without further processing. In addition, the remaining $C_7$+ material is an even better reforming feed than the prior art C₅+ material. The overall performance of the reforming zone is thus also improved in terms of octane number and yield loss.

Zone 30 is a catalytic reforming zone, but could alternatively be an aromatization zone. Catalytic reforming is described in Part 4 of HANDBOOK OF PETROLEUM REFINING, 2.sup.nd edition, by Robert A. Meyers, McGraw Hill, 1996. The reforming zone may employ a catalyst comprising platinum and tin on alumina or platinum on a zeolite, such as L-zeolite. This catalyst may be retained in fixed, moving or fluidized beds or a combination of these reactor types. Further information is provided in U.S. Pat. No. 6,001,241; U.S. Pat. No. 6,013,173 and U.S. Pat. No. 6,036,845. All four of these references are incorporated for their description of catalytic reforming.

The separation step of the subject process can be performed in a single large bed of adsorbent or in several parallel beds on a swing bed basis. However, it has been found that simulated moving bed adsorptive separation provides several advantages such as high purity and recovery. Therefore, many commercial scale petrochemical separations especially for the recovery of mixed paraffins are performed using simulated countercurrent moving bed (SMB) technology. The previously sited references are incorporated for their teaching on the performance of this process. Further details on equipment and techniques for operating an SMB process may be found in U.S. Pat. No. 3,208,833; U.S. Pat. No. 3,214,247; U.S. Pat. No. 3,392,113; U.S. Pat. No. 3,455,815; U.S. Pat. No. 3,523,762; U.S. Pat. No. 3,617,504; U.S. Pat. No. 4,006,197; U.S. Pat. No. 4,133,842; and U.S. Pat. No. 4,434,051. A different type of simulated moving bed operation which can be performed using similar equipment, adsorbent and conditions but which simulates cocurrent flow of the adsorbent and liquid in the adsorption chambers is described in U.S. Pat. No. 4,402,832 and U.S. Pat. No. 4,498,991.

Operating conditions for the adsorption chamber used in the subject invention include, in general, a temperature range of from about 20° to about 250° C., with one specific embodiment being from about 60° to about 200° C. Another embodiment includes temperatures from 90° to 160° C. Adsorption conditions also include a pressure sufficient to maintain the process fluids in liquid phase; which may be from about atmospheric to about 600 psig. Desorption conditions generally include the same temperatures and pressure as used for adsorption conditions. A/Fn is in the range of about 0.90 to about 0.92 as explained above. The practice of the subject invention requires no significant variation in operating conditions or desorbent composition within the adsorbent chambers. That is, the adsorbent preferably remains at the same temperature throughout the process during both adsorption and desorption.

The adsorbent used in the first adsorption zone preferably comprises silica alumina molecular sieves having relatively uniform pore diameters of about 5 Å. This is provided by commercially available type 5A molecular sieves produced by the adsorbents group of UOP LLC.

A second adsorbent which could be used in the adsorption zone comprises silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," NATURE, Vol. 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6 Å circular and 5.1-5.7 Å elliptical on the major axis.

This gives silicalite great selectivity as a size selective molecular sieve. Due to its aluminum free structure composed of silicon dioxide silicalite does not show ion-exchange behavior. Thus silicalite is not a zeolite. Silicalite is also described in U.S. Pat. No. 5,262,144; U.S. Pat. No. 5,276,246 and U.S. Pat. No. 5,292,900. These basically relate to treatments which reduce the catalytic activity of silicalite to allow its use as an adsorbent.

The active component of the adsorbent is normally used in the form of particle agglomerates having high physical strength and attrition resistance. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica are generally used as binders.

The active molecular sieve component of the adsorbent will ordinarily be in the form of small crystals present in the adsorbent particles in amounts ranging from about 75 to about 100 wt-% of the particle based on volatile-free composition. Volatile-free compositions are generally determined after the adsorbent has been calcined at 900° C. in order to drive off all volatile matter. The remainder of the adsorbent will generally be the inorganic matrix of the binder present in intimate mixture with the small particles of the silicalite material. This matrix material may be an adjunct of the manufacturing process for the silicalite, for example, from the intentionally incomplete purification of the silicalite during its manufacture.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 900° C. under an inert gas purge such as nitrogen for a period of time sufficient to achieve a constant weight. For the subject process it is preferred that the water content of the adsorbent results in an LOI at 900° C. of less than 7.0% and preferably within the range of from 0 to 4.0 wt-%.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In the present invention, the desorbent may be a hydrocarbon having 12 carbon atoms. The desorbent may be normal dodecane or mixture of normal dodecane and non-normal C12 hydrocarbons. Examples of non-normal hydrocarbons include branched paraffins and aromatics having from 10 to 16 carbon atoms. The desorbent stream has been known to contain one component or a mixture of components. In one embodiment the desorbent is substantially normal dodecane with less than about 5 wt-% non-normals. In another embodiment, up to about 30 wt-% of the desorbent is non-normals such as isoparaffins and aromatics. Selecting a desorbent having primarily normal dodecane provides the advantages in the $A/F_n$ ratio discussed earlier.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process containing, respectively, an extract component and a raffinate component in higher concentrations than those found in the extract stream and the raffinate stream withdrawn from adsorbent chamber. The extract stream may be rich in the desired compound or may only contain an increased concentration. The term "rich" is intended to indicate a concentration of the indicated compound or class of compounds greater than 50 mol-%.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and II. In Zone IV desorbent is partially removed from the adsorbent by a flowing mixture of desorbent and undesired components of the feed stream. The liquid flow through Zone IV. prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer ENCYCLOPEDIA OF CHEMICAL TECHNOLOGY at page 563. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

In an SMB process, the several steps e.g. adsorption and desorption, are being performed simultaneously in different parts of the mass of adsorbent retained in the adsorbent chamber(s) of the process. If the process was being performed with more or more adsorbent beds in a swing bed system then the steps may be performed in a somewhat interrupted basis, but adsorption and desorption will most likely occur at the same time.

Example 1

Light Desorbent (85% wt. nC5/15% wt iC5)

A simulated moving bed process run was conducted to process a Naphtha feed consisting of a composition outlined in Table 1;

TABLE 1

| Composition | Wt % |
|---|---|
| nC5 | 0 |
| nC6 | 3.3 |
| nC7 | 7.0 |
| nC8 | 9.0 |
| nC9 | 8.7 |
| nC10 | 8.8 |
| nC11 | 3.6 |
| Total normal paraffins | 59.5 |

While operating at 185° C., the simulated moving bed process was able to produce a normal paraffin extracted product with a purity of that ranged from 100% to 95% normal paraffins. At a set of simulated moving bed conditions and using a corresponding simulated moving bed zone parameter A/Fn of 1.2, the simulated moving bed produced a normal paraffin product with 96% purity at a corresponding normal paraffin recovery of 94%.

Example 2

Heavy Desorbent (100% nC12)

Conducted a simulated moving bed process run to process a naphtha feed consisting of a composition outlined in Table 2;

TABLE 2

| Composition | Wt % |
|---|---|
| nC5 | 7.9 |
| nC6 | 5.0 |
| nC7 | 7.9 |
| nC8 | 8.7 |
| nC9 | 7.8 |
| nC10 | 0.3 |
| nC11 | 0 |
| Total normal paraffins | 38.4 |

While operating at 185° C., the simulated moving bed process using a 100% nC12 desorbent was able to produce a normal paraffin product with an extracted purity of that ranged from 100% to 95% normal paraffins. At an optimized set of simulated moving bed conditions using a corresponding simulated moving bed MB zone parameter $A/F_n$ of 0.92, the SMB produced product with 96.4% purity and recovery of 91.4% of available normal paraffins.

It is know that the apparent diffusivity of normal paraffins shows a sharp decrease when the number of carbon atoms in the paraffin molecule increases beyond 10, see Table 1 from Sorption Kinetics of Higher n-Paraffins in Zeolite Molecular Sieves 5A, Ind. Eng. Chem. Res. 1987. As such, employing a heavy desorbent, nC12, one would expect significant performance difference when compared with the light desorbent, nC5. Surprisingly, as shown herein, at comparable normal paraffin purity the simulated moving bed was able to reduce the $A/F_n$ by 23% and only see a difference of 2.6% in normal paraffin recovery by employing the normal dodecane desorbent. Table 3 summarizes the benefits of the nC12 desorbent.

TABLE 3

| Desorbent | A/Fn | Desorbent Circulation Rate |
|---|---|---|
| 85 wt.-% nC5 | 1.2 | Base |
| 100 wt.-% nC12 | 0.92 | 71% of Base |

The invention claimed is:

1. A process for preparing a feedstream to be charged to a steam cracking unit producing ethylene, the process comprising:
   (a) passing a process feed stream comprising $C_5$ to $C_9$ hydrocarbons including $C_5$ to $C_9$ normal paraffins into an adsorption zone of a simulated moving bed adsorptive separation zone operating at an A/Fn of about 0.90 to about 0.92 and selectively retaining normal paraffins on an adsorbent located in the adsorption zone to yield a raffinate stream comprising non-normal $C_5$ to $C_9$ hydrocarbons and hydrocarbon desorbent containing 12 carbon atoms;
   (b) passing the desorbent into a desorption zone in the simulated moving bed adsorptive separation zone as at least part of a desorbent stream and removing normal paraffins from adsorbent present in the desorption zone to yield an extract stream comprising $C_5$ to $C_9$ normal paraffins and desorbent;
   (c) separating the extract stream in an extract fractionation zone into a second process stream comprising desorbent and a third process stream comprising $C_5$ to $C_9$ normal paraffins; and
   (d) passing the third process stream into a cracking zone and producing ethylene.

2. The process of claim 1 wherein the second process stream is recycled to the simulated moving bed adsorptive separation zone as at least part of said desorbent stream.

3. The process of claim 1 wherein the raffinate stream also comprises desorbent, and the raffinate stream is separated in a raffinate fractionation zone into a fourth process stream comprising desorbent and a fifth process stream comprising non-normal $C_5$ to $C_9$ hydrocarbons.

4. The process of claim 1 wherein the extract fractionation zone comprises a flash or rectified flash separation zone.

5. The process of claim 3 wherein at least a portion of the fifth process stream is passed into a naphtha reforming zone and converted into aromatic hydrocarbons.

6. The process of claim 1 wherein the desorbent comprises at least 95 wt-% normal dodecane.

7. The process of claim 1 wherein the desorbent comprises at least 70 wt-% normal dodecane.

8. The process of claim 1 wherein the desorbent comprises at least 70 wt-% normal dodecane and the remainder non-normal $C_{12}$ hydrocarbons.

9. A hydrocarbon conversion process for producing ethylene which process comprises:
   (a) passing a process feed stream comprising $C_5$ to $C_{11}$ hydrocarbons including $C_5$ to $C_{11}$ normal paraffins and $C_5$ to $C_{11}$ non-normal paraffins into an adsorption zone of a simulated moving bed adsorptive separation zone operated at adsorption conditions, and selectively retaining normal paraffins on a quantity of a selective adsorbent located in the adsorption zone to yield a raffinate stream comprising non-normal $C_5$ to $C_{11}$ hydrocarbons and C12 hydrocarbon desorbent;
   (b) passing C12 hydrocarbon desorbent into a desorption zone, operated at desorption conditions, of the adsorptive separation zone as at least part of a desorbent stream, and removing normal paraffins from adsorbent present in the desorption zone to yield an extract stream comprising $C_5$ to $C_{11}$ normal paraffins and desorbent;
   (c) separating the extract stream in an extract fractionation zone into a second process stream comprising desorbent and a third process stream comprising $C_5$ to $C_{11}$ non-normal paraffins; and
   (d) passing at least a portion of the third stream into a cracking zone and producing ethylene.

10. The process of claim 9 wherein the raffinate stream also comprises desorbent, and the raffinate stream is separated in a raffinate fractionation zone into a fourth process stream comprising desorbent and a fifth process stream comprising non-normal $C_5$ to $C_{11}$ hydrocarbons.

11. The process of claim 9 wherein the second process stream is recycled within the process as at least a part of the desorbent stream.

12. The process of claim 10 wherein at least a portion of the fifth process stream is passed into a naphtha reforming zone and converted into aromatic hydrocarbons.

13. The process of claim 9 wherein the desorbent comprises at least 95 wt-% normal dodecane.

14. The process of claim 9 wherein the desorbent comprises at least 70 wt-% normal dodecane.

15. The process of claim 9 wherein the desorbent comprises at least 70 wt-% normal dodecane and the remainder non-normal dodecane.

16. A process for preparing the feedstreams to a catalytic reforming zone and to a steam cracking unit producing ethylene, which process comprises:
(a) passing a process feed stream comprising $C_5$ to $C_9$ hydrocarbons including $C_5$ to $C_9$ normal paraffins into a simulated moving bed adsorption zone of an adsorptive separation zone operated at an A/Fn from about 0.90 to 0.92 and selectively retaining normal paraffins on an adsorbent located in the adsorption zone to yield a raffinate stream comprising $C_5$ to $C_9$ non-normal hydrocarbons;
(b) passing desorbent selected from the group C12 hydrocarbons into a desorption zone in the adsorptive separation zone as at least part of a desorbent stream and removing normal paraffins from adsorbent present in the desorption zone to yield an extract stream comprising $C_5$ to $C_9$ normal paraffins and desorbent;
(c) separating the extract stream in a extract fractionation zone into a second process stream comprising desorbent and a third process stream comprising $C_5$ to $C_9$ normal paraffins;
(d) passing the third process stream into a cracking zone and producing ethylene;
(e) separating at least a portion of the raffinate stream in a raffinate fractionation zone into a fourth process stream comprising desorbent and a fifth process stream comprising $C_5$ to $C_9$ non-normal hydrocarbons; and
(f) passing the fifth process stream into a catalytic reforming zone operated at reforming conditions.

17. The process of claim 16 wherein the desorbent comprises at least 95 wt-% normal dodecane.

18. The process of claim 16 wherein the desorbent comprises at least 70 wt-% normal dodecane.

19. The process of claim 16 wherein the desorbent comprises at least 70 wt-% normal dodecane and the remainder non-normal $C_{12}$ hydrocarbons.

20. The process of claim 16 wherein the second and fourth process streams are recycled to the adsorptive separation zone.

* * * * *